(12) United States Patent
Calvert et al.

(10) Patent No.: US 11,305,070 B2
(45) Date of Patent: Apr. 19, 2022

(54) NEEDLE COVER

(71) Applicant: Owen Mumford Limited, Oxford (GB)

(72) Inventors: Jack Calvert, Oxford (GB); Rosie Hutt, Oxford (GB)

(73) Assignee: Owen Mumford Limited, Oxford (GB)

( * ) Notice: Subject to any disclaimer, the term of this patent is extended or adjusted under 35 U.S.C. 154(b) by 265 days.

(21) Appl. No.: 16/494,025

(22) PCT Filed: Mar. 8, 2018

(86) PCT No.: PCT/GB2018/050592
§ 371 (c)(1),
(2) Date: Sep. 13, 2019

(87) PCT Pub. No.: WO2018/167463
PCT Pub. Date: Sep. 20, 2018

(65) Prior Publication Data
US 2020/0086062 A1 Mar. 19, 2020

(30) Foreign Application Priority Data
Mar. 15, 2017 (GB) ..................................... 1704138

(51) Int. Cl.
*A61M 5/32* (2006.01)
*A61M 5/31* (2006.01)

(52) U.S. Cl.
CPC ........ *A61M 5/3257* (2013.01); *A61M 5/3134* (2013.01); *A61M 5/3202* (2013.01);
(Continued)

(58) Field of Classification Search
CPC .............. A61M 5/3134; A61M 5/3202; A61M 2005/3254; A61M 2005/3247
(Continued)

(56) References Cited

U.S. PATENT DOCUMENTS 4,908,023 A * 3/1990 Yuen ................... A61M 5/3271
604/110
2010/0042047 A1 2/2010 Suzuki
(Continued)

FOREIGN PATENT DOCUMENTS

| EP | 2839854 A1 | 2/2015 | |
| EP | 3478343 B1 * | 1/2021 | ........ A61M 5/31536 |
| WO | 2016181127 A1 | 11/2016 | |

OTHER PUBLICATIONS

International Search Report and Written Opinion, International Application No. PCT/GB2018/050592, dated Jun. 18, 2018, 10 pages.
(Continued)

*Primary Examiner* — Bhisma Mehta
*Assistant Examiner* — Nidah Hussain
(74) *Attorney, Agent, or Firm* — Quarles & Brady LLP

(57) ABSTRACT

A needle protection device (10) for protecting a needle has a needle carrier (12) for carrying said needle (14) and being translatable along a longitudinal axis X between a first, deployed, position (D) and a second, protected, position (P); a shuttle (16) surrounding said needle (14); a hub (24) for receiving the needle carrier (12); a sleeve (26) being rotatable around each of said needle carrier (12), said shuttle (16) and said hub (24); a first driving mechanism (30) between said needle carrier (12) and said shuttle (16) to cause axial displacement of said shuttle (16) in a first direction (A) between a first, retracted position R and a second, deployed position Ds upon axial displacement of the needle carrier (12) along axis X; and a second driving mechanism (32) between said needle carrier (12) and said sleeve (26) to cause axial displacement of the carrier (12) in said first direction (A) upon rotational displacement of the sleeve (26).

19 Claims, 6 Drawing Sheets

(52) U.S. Cl.
CPC ... *A61M 5/3271* (2013.01); *A61M 2005/3247* (2013.01); *A61M 2005/3254* (2013.01)

(58) Field of Classification Search
USPC ........................................................ 604/198
See application file for complete search history.

(56) References Cited

U.S. PATENT DOCUMENTS

| | | |
|---|---|---|
| 2010/0234881 A1 | 9/2010 | Blaeser et al. |
| 2011/0178473 A1 | 7/2011 | Richards et al. |
| 2016/0361505 A1 | 12/2016 | Bengtsson et al. |

OTHER PUBLICATIONS

Combined Search and Examination Report, GB Application No. GB1704138.5, dated Aug. 15, 2017, 7 pages.

\* cited by examiner

NEEDLE COVER

CROSS-REFERENCE TO RELATED APPLICATIONS

This application represents the U.S. National Stage of International Application No. PCT/GB2018/050592 filed Mar. 8, 2018, which claims priority to British Patent Application Serial No. GB 1704138.5, filed Mar. 15, 2017, and entitled, "A Needle Cover", all of which are incorporated herein by reference in their entirety.

FIELD OF THE INVENTION

The present invention relates to a needle shroud and relates more particularly to a lockable shroud such as may be used in relation to a needle assembly used in the delivery of fluids to a human or animal patient. Such needle assemblies are typically configured for attachment to an injection device, cartridge or syringe.

BACKGROUND OF THE INVENTION

Injection devices, such as the Owen Mumford Autopen®, are commonly used by patients to self-administer injections of medicament. Such devices are typically provided in a pen-like body which contains, defines or receives a cartridge or syringe of medicament. The injection device generally comprises a delivery mechanism which is arranged to dispense the medicament via a needle in response to a user pressing a button or trigger.

Many such injection devices are arranged to be either reusable i.e. the cartridge of medicament can be replaced or to deliver a plurality of separate injections until the medicament within the device has been fully consumed. It is also common to arrange the device to receive a disposable, single-use, needle assembly. Such needle assemblies are generally referred to as "pen needles".

Pen needles comprise a body or hub which is configured to be attached to the injection device in use for example by means of a screw thread or other removable attachment arrangement and which supports the needle. Typically, the needle is a double ended needle having a forward end for use in penetrating a user's skin and a rearward end which pierces a septum of a cartridge or syringe in the injection device when the pen needle is attached to the device. It will be appreciated that such syringe/cartridge septa are self-sealing membranes which can maintain the sealing and sterility of the syringe/cartridge over a number of uses. A primary container may also be provided which initially covers the needle to provide protection against needle stick injuries and to maintain sterility of the needle and the needle assembly may initially be sealed within the cap by means of removable sterile packaging.

It is known to provide needle assemblies such as pen needles with a shroud which is arranged to cover the needle after use and in some cases also prior to use to reduce the risk of accidental needle-stick injuries after use or during disposal of the needle assembly. For example, one form of needle assembly may include a shroud which is arranged to telescope forwardly relative to the hub after use to cover the forward end of the needle. An alternative arrangement may include a simple cap to be placed over the sharp end of the needle when not in use. Whilst such shrouds provide excellent protection for a patient from the sharp end of the needle it has been found that still further protection can be provided, particularly after supply of fluid to be delivered has been exhausted and the assembly must be disposed of.

Embodiments of the invention seek to provide improved needle assemblies which may improve on the above arrangements.

SUMMARY OF THE INVENTION

Accordingly, the present invention provides a needle protection device for protecting a needle having a first end and a second end comprising: a needle carrier for carrying said needle, having a first end and a second end, an outer surface and a longitudinal axis X and being translatable along said longitudinal axis X between a first, deployed, position D and a second, protected, position P; a shuttle surrounding said needle, having a first end and a second end, a longitudinal axis X, a longitudinally extending inner aperture for receiving said needle, an inner opening having a surface for receiving said needle carrier and an outer surface; a hub for receiving the needle carrier; a sleeve having a first end a second end and an inner surface surrounding and being rotatable around each of said needle carrier, said shuttle and said hub; and a first driving mechanism between said needle carrier and said shuttle to cause axial displacement of said shuttle in a first direction A between a first, retracted position R and a second, deployed position Ds upon axial displacement of the needle carrier along axis X; and a second driving mechanism between said needle carrier and said sleeve to cause axial displacement of the carrier in said first direction A upon rotational displacement of the sleeve.

In a preferred arrangement said first driving mechanism comprises a first cam on the needle carrier and a first cam follower on the inner aperture of the shuttle.

In a particular arrangement said first cam comprises a longitudinally extending spiral cam and wherein said cam follower comprises a longitudinally extending spiral cam follower.

In a particular arrangement said cam comprises a protrusion projecting from the outer surface of the needle carrier and wherein said cam follower comprises a recess extending into the inner surface of the inner aperture.

The device may include a first anti-rotation mechanism between the shuttle and the sleeve such as to prevent the shuttle rotating upon rotation of the sleeve. The first anti-rotation mechanism may comprise a longitudinally extending slot within the outer surface of the shuttle and a corresponding projection at the first end of the inner surface of the sleeve. Alternatively, the anti-rotation mechanism may comprise a pair of longitudinally extending slots within the outer surface of the shuttle and a pair of corresponding projections at the first end of the inner surface of the sleeve.

The second driving mechanism may comprise a protrusion on the outer surface of the needle carrier and a longitudinally extending first spiral slot on the inner surface of the sleeve. Alternatively, the second driving mechanism may comprise a pair of protrusions on the outer surface of the needle carrier and a pair of longitudinally extending first spiral slots on the inner surface of the sleeve.

The arrangement may include a second anti-rotation mechanism between the hub and the needle carrier such as to prevent the needle carrier rotating relative to the hub during axial translation of the needle carrier. The second anti-rotation mechanism may include a radially extending base portion having a radially outer edge and being secured to the second end of the needle carrier, one or more axially extending slots at said outer edge and one or more axially extending projections extending from said hub and passing through said one or more axially extending slots such that said base portion slides along said one or more extension portions upon rotational movement of the sleeve.

The arrangement may further include a retaining mechanism for retaining the axial position of the sleeve relative to the hub. Said retaining mechanism may comprise a radially extending recess extending around an outer circumference of the hub and a radially extending projection extending around an inner circumference of said inner surface of the sleeve. The retaining mechanism may comprise a click-fit fitting having first and second interlocking surfaces which, between them, prevent the sleeve being removed from the hub.

The hub may include a first end, a second end, an inner void at said second end and an aperture extending through said hub between said inner void and said first end.

The needle may be mounted within the needle carrier such that the first end of the needle extends beyond the first end of the needle carrier and the second end of the needle may extend beyond the second end of the needle carrier (12).

The first end of the needle extends axially beyond the first end of the shuttle when in a deployed position D and is contained within the shuttle when in a second protected position P.

The second end of the needle may extend into said inner void when in a deployed position D and may be contained within aperture when in a second protected position P.

In a first position of the needle carrier the second end of the needle may extend into the inner void and in a second position does not extend into said inner void.

DESCRIPTION OF EMBODIMENTS

In the following embodiments, the terms "front" or "first end" refer to the patient facing end of the needle assembly or component thereof. In other words, the front end of the needle assembly is the end proximal to the injection site during use. Likewise, the terms "rear" or "second end" refer to the non-patient end of the needle assembly or component thereof. In other words, the terms "rear" or "second" mean distant or remote from the injection site during use.

Axial, radial and circumferential are used herein to conveniently refer to the general directions relative to the longitudinal direction of the needle assembly or components thereof. The skilled person will, however, appreciated that these terms are not intended to be narrowly interpreted and for example, the needle assembly may have a non-circular and/or irregular form. Typically, regardless of the chosen needle assembly external profile the needle will have a conventional generally cylindrical elongate hollow form and the longitudinal axis X of the needle assembly will substantially coincide with or be parallel to the axial direction of the needle.

Figure 1:
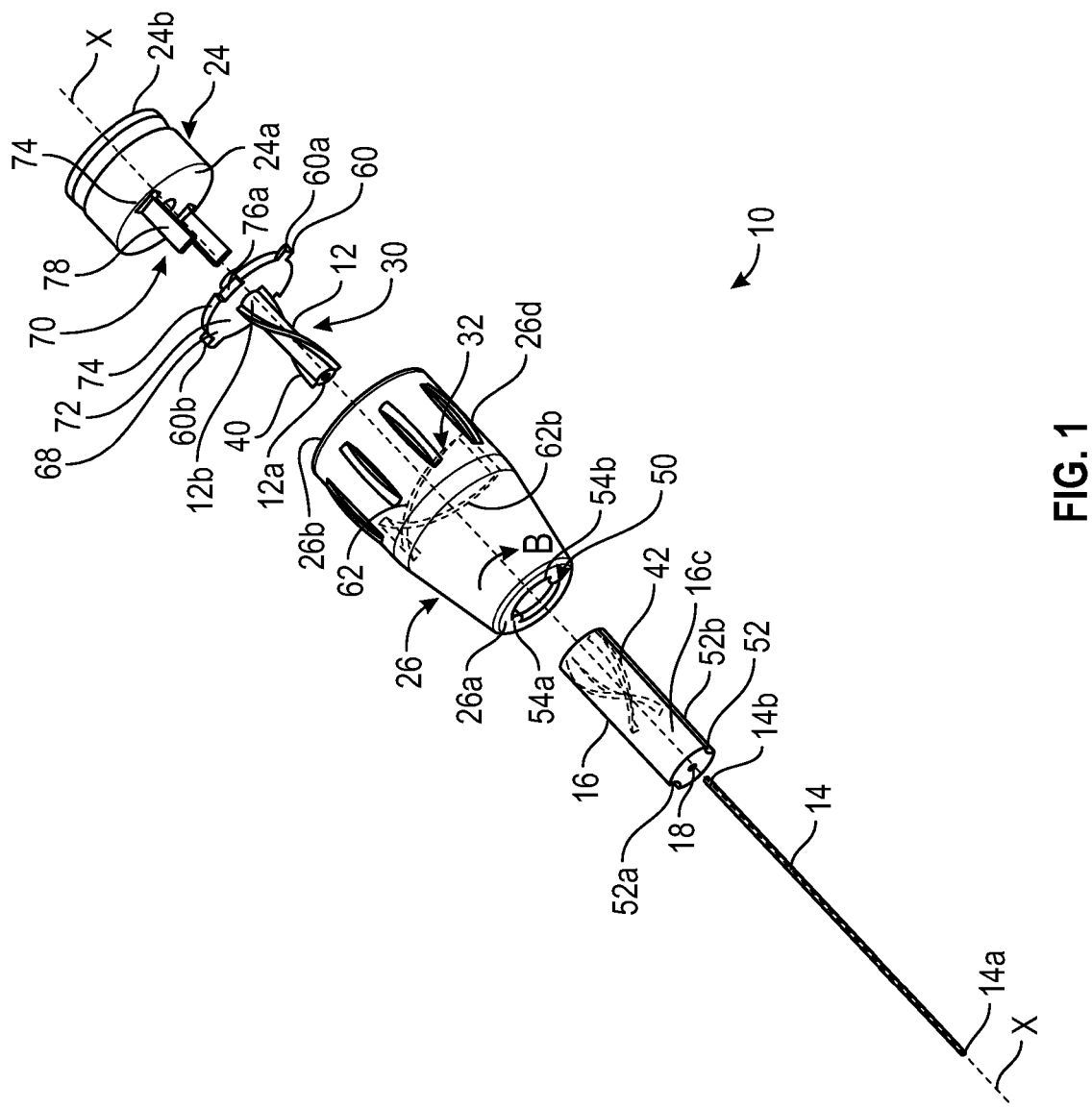
FIG. 1 is an exploded view of the needle protection device in accordance with the present invention.
Figure 2:
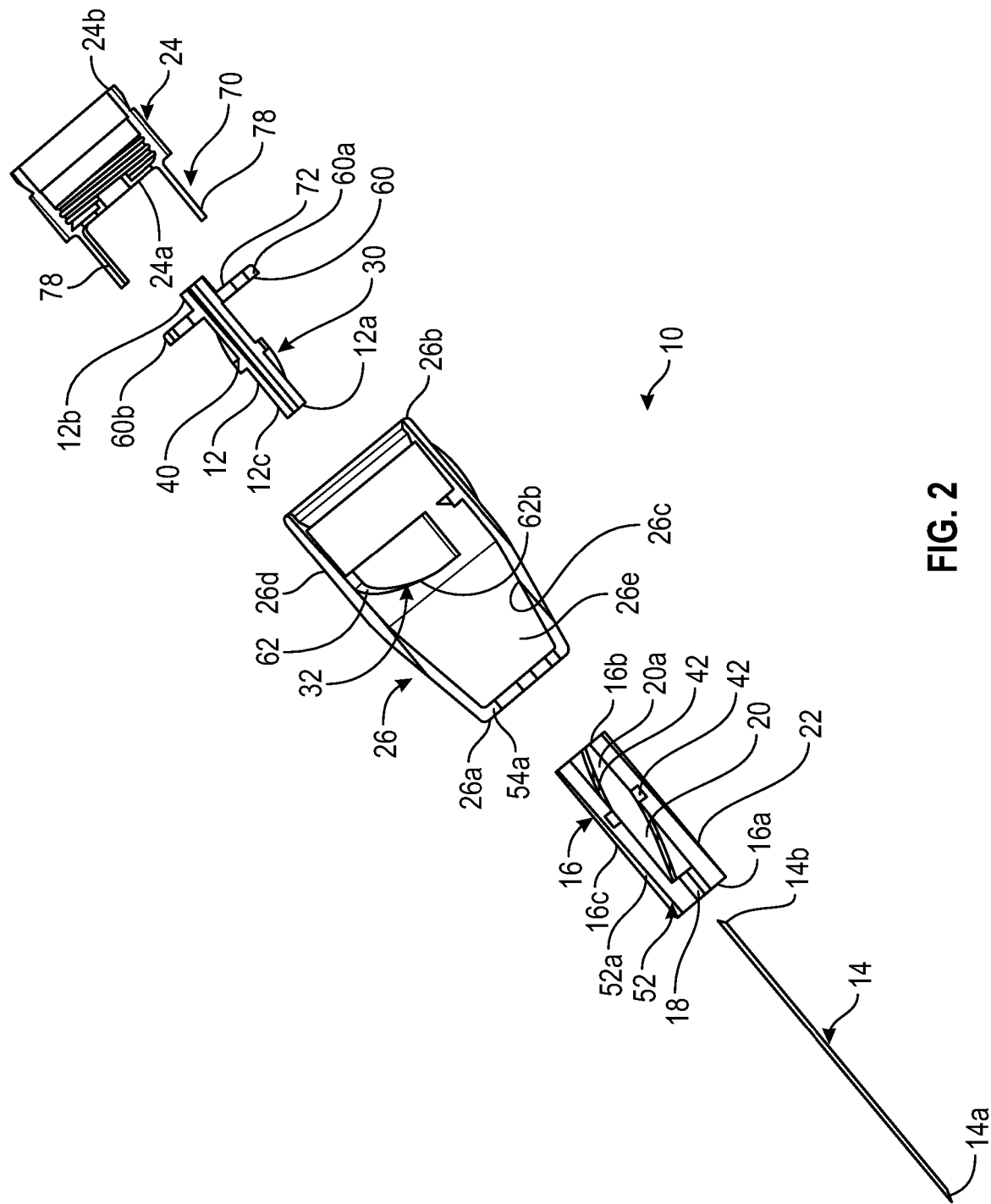
FIG. 2 is a cross-sectional view of the assembly shown in FIG. 1.
Figure 3:
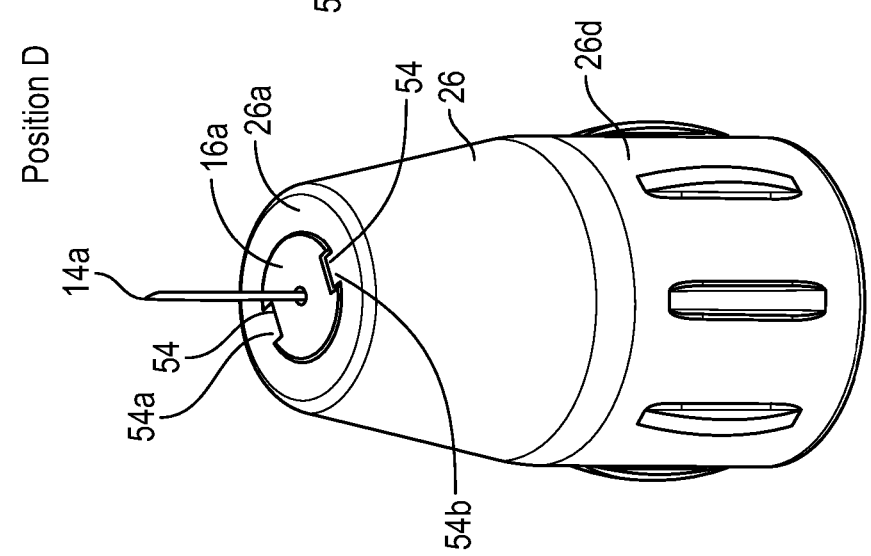
Figure 6:
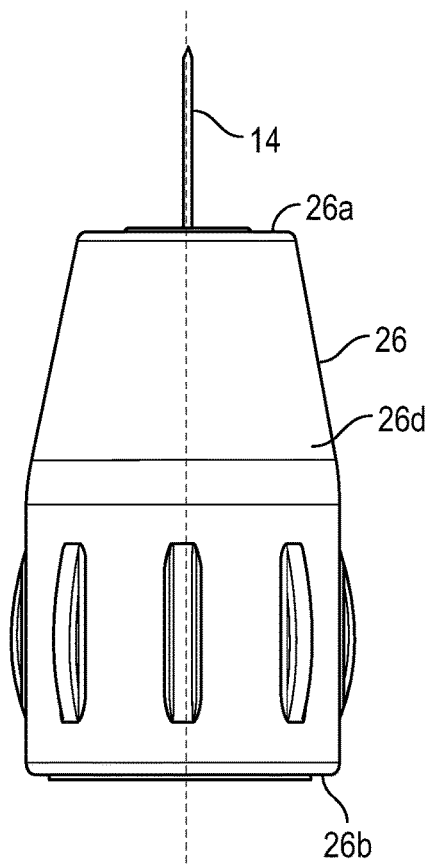
FIG. 6 is a side elevation of the arrangement of FIG. 3.
Figure 7:
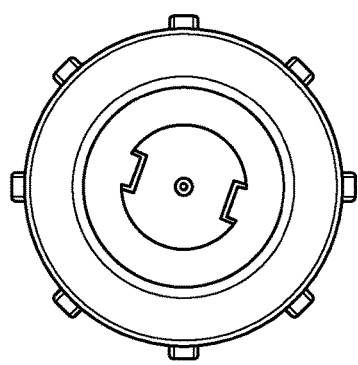
FIG. 7 is a plan view of the arrangement of FIG. 3.
Figure 8:
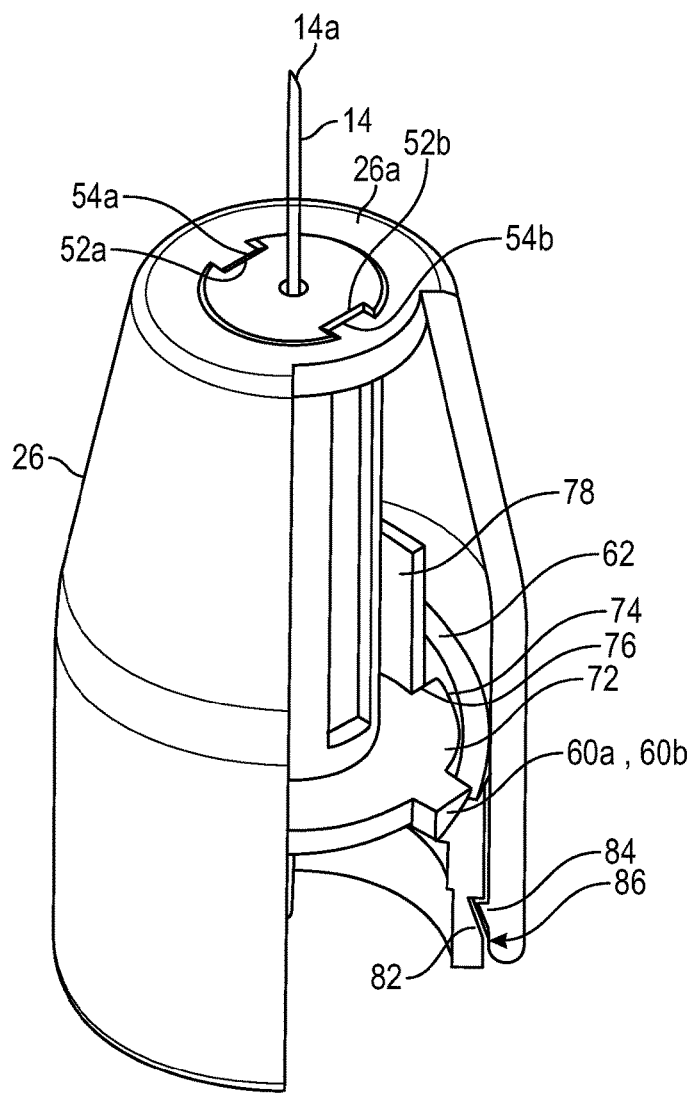
FIG. 8 is a partial cut-away view of the arrangement of FIG. 3.

Referring now to the drawings in general but particularly to FIGS. 1 to 3, a needle protection device 10, commonly referred to as a shroud, is shown in exploded form in FIG. 1 and includes a needle carrier 12 for carrying a needle 14 having a first end 14a and a second end 14b, a shuttle 16 surrounding the needle and being movable between a first, retracted position and a second, deployed position and a hub 24 for receiving said needle carrier 12 and preventing rotation thereof whilst allowing axial translation thereof. The needle 14 is usually bonded into the carrier 12 or is retained therein by means of frictional contact.

A sleeve shown generally at 26 surrounds the carrier 12 and shuttle 16 and is operably connected to both the carrier 12 and the shuttle 16 such that rotational movement of the sleeve 26 causes axial movement of the carrier 12 and/or the shuttle 16.

A first drive mechanism 30, described in detail later herein, is provided between said needle carrier 12 and said shuttle 16 to facilitate the desired movement.

A second drive mechanism 32, also described in more detail later herein, is provided between the carrier 12 and the sleeve 26 for causing the desired movement. The needle carrier 12 has a first end 12a and a second end 12b, an outer surface 12c and extends along and is translatable along the longitudinal axis X of the device 10 between a first deployed position D, where the needle is exposed and a second protected position P. where the needle is covered.

The shuttle 16 has a first end 16a and a second end 16b, an outer surface 22, a longitudinally extending axis X, a longitudinally extending inner aperture 18 extending into the first end 16a for receiving said needle 14 and an inner opening 20 at said second end 16b having an inner surface 20a for receiving the needle carrier 12 and first driving mechanism 30.

A first anti-rotation mechanism, shown generally at 50 and described in more detail later herein is provided between the shuttle 16 and the sleeve 26 such as to prevent rotation of the shuttle 16 relative to the sleeve 26.

The sleeve 26 has a first end 26a, a second end 26b, an inner surface 26c and an outer surface 26d and further includes an inner aperture 26e for receiving both the shuttle 16 and the needle carrier 12. The shuttle 16 is received into aperture 26e at the second end of the sleeve 26b whilst the needle carrier 12 is received into the aperture 26d at the first end of the sleeve 26a. The sleeve 26 effectively surrounds each of the shuttle 16 and needle carrier 12 whilst interacting with the needle carrier 12 via the second drive mechanism 32 which causes axial displacement of the needle carrier 12 upon rotation of the sleeve 26.

The hub 24 has a first end 24a for receiving the needle carrier 12, a second end 24b and an inner void 24c at said second end 24b and an aperture 24d extending through said hub 24 in the direction of axis X between the inner void 24c and said first end 24a and is coupled at its first end 24a to the second end 12b of the needle carrier 12 by means of a second anti-rotation mechanism, shown generally at 70 and described in more detail later herein. The inner void 24c may also include an inner surface 24s including a securing mechanism 24m such as, for example, a screw thread for securing said hub 24 to an outlet end of a fluid container in a manner well known to those skilled in the art and, therefore, not described further herein. It will be appreciated that other mechanisms to couple the hub 24 to a container may also be used.

The hub 24 may also include a retaining mechanism, shown generally at 80 (FIG. 9), for causing the retention of the sleeve 26 on the hub 24. Such a mechanism 80 may comprise a circumferentially extending recess 82 extending around an outer circumference of the hub 24 and a radially extending projection 84 extending around an inner circumference of said inner surface 26c of the sleeve 26. In a preferred arrangement, the retaining mechanism 80 comprises a "click-fit" fitting 86 having first and second interlocking surfaces 88a, 88b which, between them, prevent the sleeve 26 being removed from the hub 24.

The first drive mechanism 30 may comprise a first cam 40 on the needle carrier 12 and a first cam follower 42 on the inner surface 20a of the shuttle 16 and may particularly comprise a longitudinally extending spiral cam and said cam follower 42 may particularly comprise a longitudinally extending spiral cam follower. In a preferred arrangement said cam 40 comprises a protrusion 40a projecting from the outer surface 12c of the needle carrier 12 and said cam follower 42 comprises a recess 42a extending into the inner surface 20a of the inner aperture 20. It will, however, be appreciated that other forms of cam arrangement may be used so long as the same function is achieved. The pitch of the spiral cam is selected to be of a coarse pitch having a pitch angle of $\theta^1$ such as to achieve a significant axial output movement for a relatively small axial input movement.

The second drive mechanism 32 may comprise a protrusion 60 on the outer surface 12c of the needle carrier 12 and a longitudinally extending first spiral slot 62 on the inner surface 26c of the sleeve 26. Alternatively, said second driving mechanism 32 may comprise a pair of protrusion 60a, 60b on the outer surface 12c of the needle carrier 12 and a pair of longitudinally extending first spiral slots 62a, 62b on the inner surface 26c of the sleeve 26. It will be appreciated that other forms of drive mechanism may be employed. The pitch of the spiral slots is selected to be of a pitch having a pitch angle $\theta^2$ which is less coarse than that of the first drive mechanism such as to achieve a relatively small axial movement of the needle carrier 12 for a given radial movement of the sleeve 26.

The first anti-rotation mechanism 50 may comprise a longitudinally extending slot 52 extending in the direction of axis X within the outer surface 16c of the shuttle 16 and a corresponding projection 54 at the second end 26b of the sleeve 26. Alternatively, the anti-rotation mechanism 50 may comprise a pair of longitudinally extending slots 52a, 52b within the outer surface 16c of the shuttle 16 and a pair of corresponding projections 54a, 54b at the first end 26a of the inner surface 26c of the sleeve 26. It will, however, be appreciated that other forms of anti-rotation mechanism may be used so long as they perform the same function.

The second anti-rotation mechanism 70 may include a radially extending base portion 72 on the needle carrier 12 having a radially outer edge 74 secured to, for example, the second end 12b of the needle carrier 12, one or more axially extending slots 76 at said outer edge 74 and one or more axially extending projections 78. The projections extend axially in the direction of axis X from the first end 24a of said hub 24 and pass through said one or more axially extending slots 76 such that said base portion 72 slides along said one or more extension portions 76 upon rotational movement of the sleeve 26. In the preferred arrangement there are provided a pair of projections 78a, 78b and a pair 76a, 76b of slots.

Figure 5:
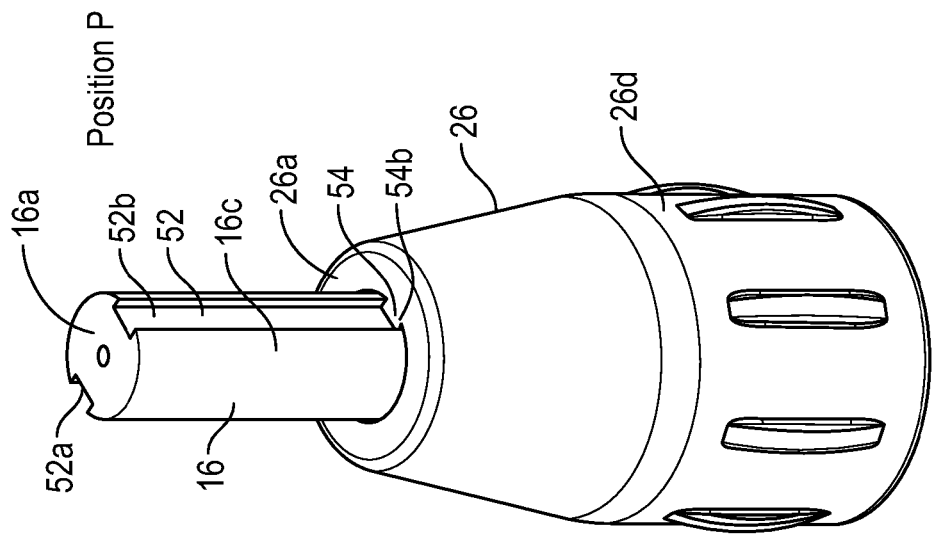
FIGS. 3, 4 and 5 are views of the end portion of the device of FIGS. 1 and 2 and illustrate the needle in each of the retracted, part deployed and fully deployed positions.
Figure 4:
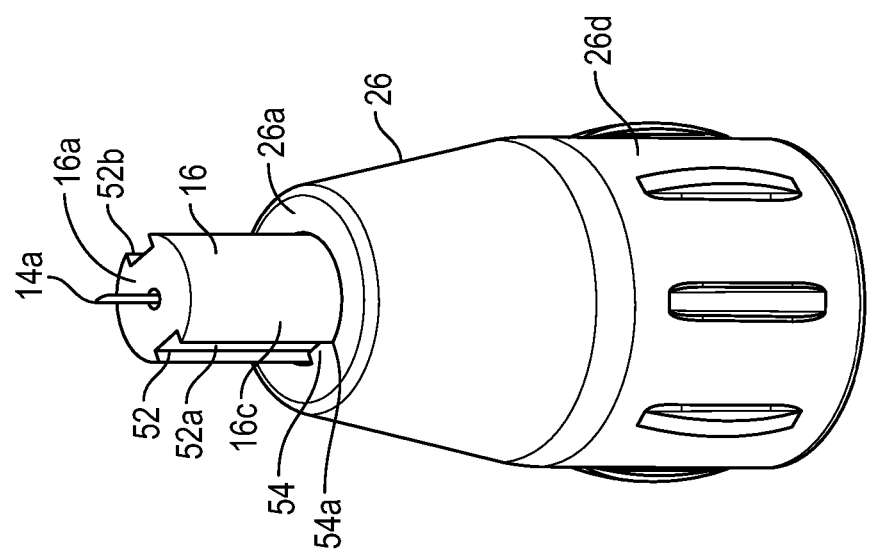
Figure 10:
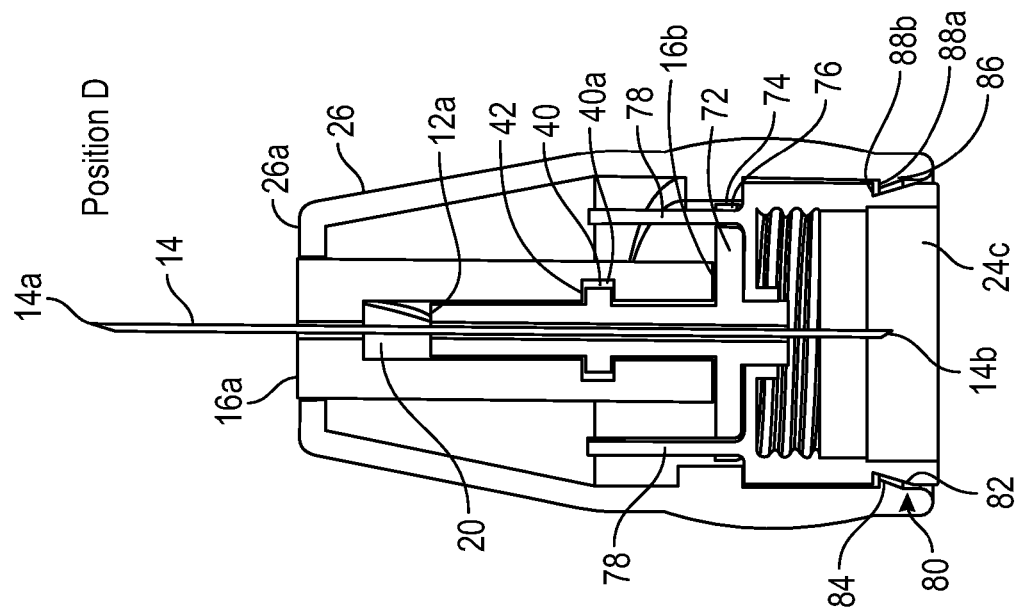
FIGS. 10, 11 and 12 are second cross-sectional views respectively of the arrangements in FIGS. 3 to 5 and illustrate the inter-relationship of components within the device when in each of the retracted, part deployed and fully-deployed positions.
Figure 12:
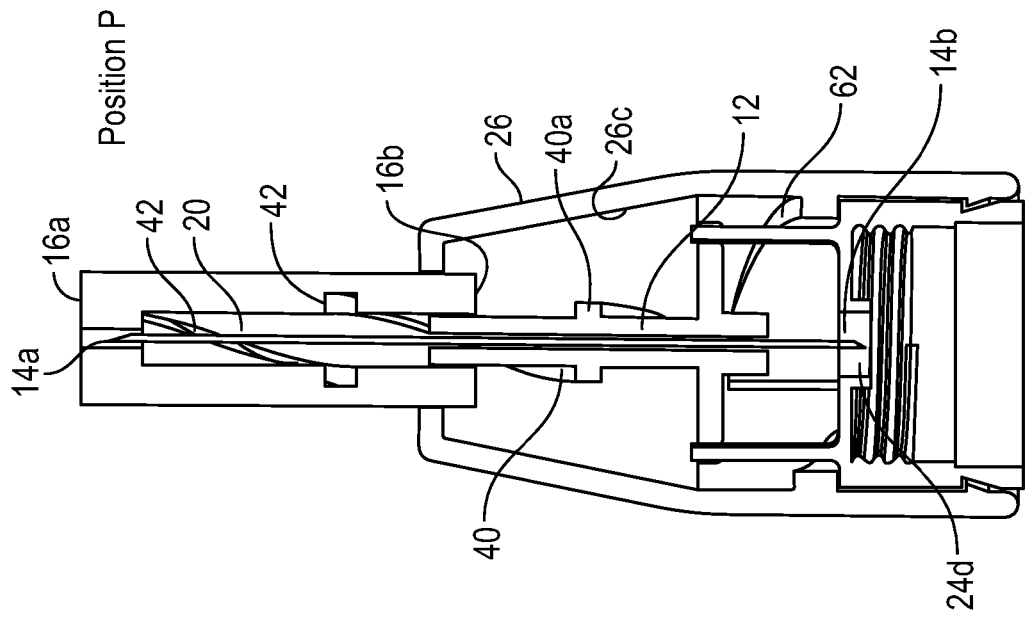
Figure 11:
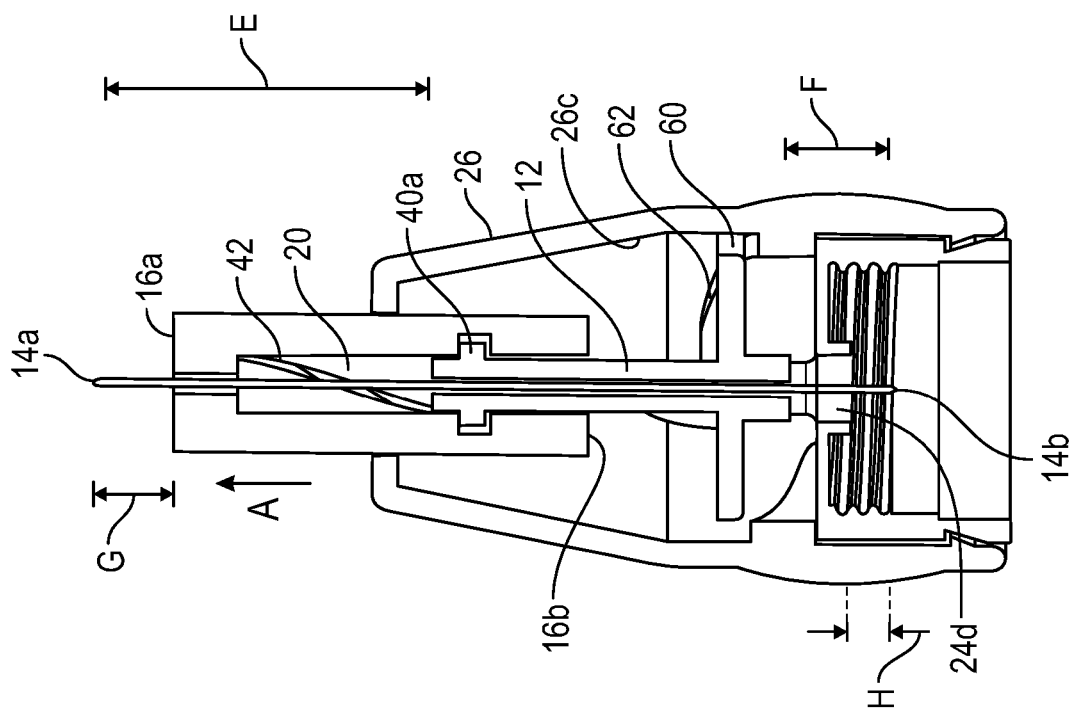

Operation of the above device 10 will now be described by way of example only with reference to the drawings in general but with particular reference to FIGS. 3 to 5 and 10 to 12 which, between themselves, show the movement of the components between a retracted position (FIGS. 3 and 10) and a deployed position (FIGS. 5 and 12). FIGS. 3 and 10 show the device with the needle 14 exposed whilst FIGS. 5 and 12 show the shuttle 16 covering and protecting the needle.

Figure 9:
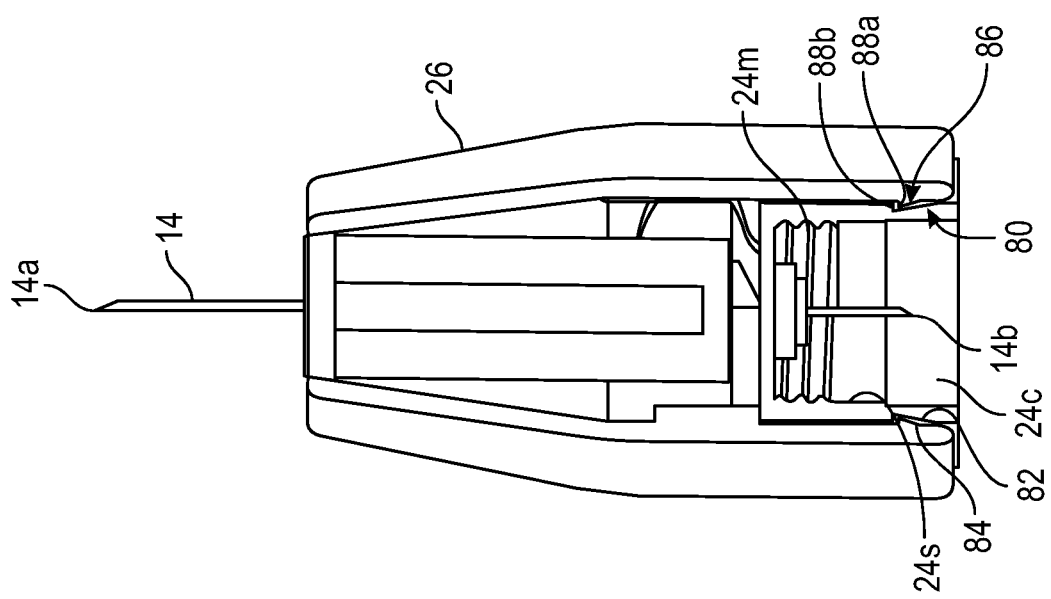
FIG. 9 is a first cross-sectional view of the arrangement of FIG. 3.

From FIGS. 3 and 9 it will be appreciated that when the needle 14 is fully exposed the second end 16b of shuttle 16 rests on the radially extending base portion 72 and the shuttle 16 lies generally within the sleeve 26 whilst projections 60a and 60b rest upon a lower portion the cam surface 62. Rotation of sleeve 26 in the direction of arrow B of FIG. 1 will cause activation of the second drive mechanism 32 causing the projections 60a, 60b and needle carrier 12 to rise up the surface of cam 62 whilst being guided by the constraints of the second anti-rotation mechanism 70 and as they do so they will take the attached needle 14 with them. This action causes end 14b of needle 14 to be withdrawn from within the void 24c of the hub 24 and up towards opening 24d. The action also causes the first drive mechanism 30 to be activated by the interaction of cam 40 acting on cam follower 42. As the shuttle 16 is prevented from rotation by means of the first anti-rotation mechanism 50, axial movement of the needle carrier 12 will operate cam 40 such as to push cam follower 42 and the shuttle itself 16 axially in the direction of arrow A in FIG. 11. Such axial movement of the shuttle 16 will cause the shuttle to move towards a position in which it is starting to cover the needle 14 but this will only be possible if the pitch of the cam 42 is greater than that of cam 62. Continuing rotation of sleeve 26 will impart more axial movement on the needle carrier 12 which then translates to further axial movement of the shuttle. Eventually, the shuttle 16 will reach an axial position (best seen in FIGS. 5 and 12 where it completely covers the needle 14 and, thereby, protects any patient or medical staff from the end of the needle itself.

From the drawings it will be appreciated that said needle 14 is mounted within the needle carrier 12 such that the first end 14a of the needle extends beyond the first end 12a of the needle carrier 12 by an amount E and the second end of the needle 14b extends beyond the second end 12b of the needle carrier 12 by an amount F. it will also be appreciated that the first end 14a of the needle 14 extends axially beyond the first end 16a of the shuttle 16 by an amount G when in a deployed position D and is contained within the shuttle 16 when in a second protected position P. Still further, it will be appreciated that the second end 14b of the needle extends into said inner void 24c by an amount H when in a deployed position D and is contained within aperture 24d when in a second protected position P and that in a first position of the needle carrier 12 the second end 14b of the needle extends into the inner void 24c and in a second position does not extend into said inner void 24c.

It will be appreciated that reversal of the rotational movement in the opposite direction of arrow B in FIG. 1 will cause reversal of the movements of the needle carrier 12 and also the shuttle 16 and complete reversal of the motion will cause the first end of the needle 14a to become completely exposed and the second end of the needle to be returned into void 24c such as to allow the needle to receive fluid from any container or vessel connected to the second end 24b of the hub 24. In the proposed/preferred operation of the device it is operated such as to latch/lock the shuttle (and thus the needle carrier) in the protected position, such that the safety pen needle is a single use device.

It will also be appreciated that the first position of the device may be when the needle is fully exposed or when the needle is fully protected.

Still further, it will be appreciated that the components of the device may each be made of a mouldable plastics material or may be machined or formed in metal.

It will also be appreciated that a "click-fit" fitting is one which makes use of inter-engaging features which are engaged with each other by deformation of one or other thereof during an assembly process.

The invention claimed is:

1. A needle protection device for protecting a needle having a first end and a second end comprising:
   a) a needle carrier for carrying said needle, said needle carrier having a first end and a second end, an outer surface and a longitudinal axis X and being translatable along said longitudinal axis X between a first, deployed position and a second, protected, position;
   b) a shuttle surrounding said needle carrier, having a first end and a second end, a longitudinal axis X, a longitudinally extending inner aperture for receiving said needle, an inner opening having a surface for receiving said needle carrier and an outer surface;
   c) a hub for receiving the needle carrier;
   d) a sleeve having a first end, a second end, and an inner surface surrounding and being rotatable around each of said needle carrier, said shuttle and said hub;
   e) a first driving mechanism comprising a spiral cam on one of said needle carrier and said shuttle and a cam follower on the other side of said needle carrier and said shuttle; and
   f) a second driving mechanism comprising a spiral slot on one side of said needle carrier and said sleeve and a protrusion on the other side of said needle carrier and said sleeve,
   wherein rotational displacement of the sleeve causes axial displacement of the carrier in a first direction which translates to axial displacement of said shuttle in said first direction between a first retracted position and a second deployed position,
   wherein the rotational displacement of the sleeve does not cause axial displacement of the hub relative to the sleeve, and
   wherein the pitch of the cam of the first drive mechanism is greater than the pitch of the slot of the second drive mechanism.

2. A needle protection device as claimed in claim 1, wherein the spiral cam is on the needle carrier and the cam follower is on the inner aperture of the shuttle.

3. A needle protection device as claimed in claim 2, wherein the spiral cam comprises a longitudinally extending spiral cam and wherein said cam follower comprises a longitudinally extending spiral cam follower.

4. A needle protection device as claimed in claim 3, wherein said spiral cam comprises a protrusion projecting from the outer surface of the needle carrier and wherein said cam follower comprises a recess extending into the inner surface of the inner opening.

5. A needle protection device as claimed in claim 1 and including a first anti-rotation mechanism between the shuttle and the sleeve such as to prevent the shuttle rotating upon rotation of the sleeve.

6. A needle protection device as claimed in claim 5, wherein the first anti-rotation mechanism comprises a longitudinally extending slot within the outer surface of the shuttle and a corresponding projection at the first end of the inner surface of the sleeve.

7. A needle protection device as claimed in claim 5, wherein the anti-rotation mechanism comprises a pair of longitudinally extending slots within the outer surface of the shuttle and a pair of corresponding projections at the first end of the inner surface of the sleeve.

8. A needle protection device as claimed in claim 1, wherein said second driving mechanism comprises the protrusion on the outer surface of the needle carrier and the spiral slot on the inner surface of the sleeve.

9. A needle protection device as claimed in claim 8 and including a second anti-rotation mechanism between the hub and the needle carrier such as to prevent the needle carrier rotating relative to the hub during axial translation of the needle carrier.

10. A needle protection device as claimed in claim 9, wherein said second anti-rotation mechanism includes a radially extending base portion having a radially outer edge and being secured to the second end of the needle carrier, one or more axially extending slots at said outer edge and one or more axially extending projections extending from said hub and passing through said one or more axially extending slots such that said base portion slides along said one or more extension portions upon rotational movement of the sleeve.

11. A needle protection device as claimed in claim 1, wherein said second driving mechanism comprises a pair of protrusions including the protrusion on the outer surface of the needle carrier and a pair of longitudinally extending first spiral slots including the spiral slot on the inner surface of the sleeve.

12. A needle protection device as claimed in claim 1 and further including a retaining mechanism for retaining the axial position of the sleeve relative to the hub.

13. A needle protection device as claimed in claim 12, wherein said retaining mechanism comprises a radially extending recess extending around an outer circumference of the hub and a radially extending projection extending around an inner circumference of said inner surface of the sleeve.

14. A needle protection device as claimed in claim 12, wherein said retaining mechanism comprises a click-fit fitting having first and second interlocking surfaces which, between them, prevent the sleeve being removed from the hub.

15. A needle protection device as claimed in claim 1, wherein said hub includes a first end, a second end, an inner void at said second end and an aperture extending through said hub between said inner void and said first end.

16. A needle protection device as claimed in claim 1, wherein said needle is mounted within the needle carrier such that the first end of the needle extends beyond the first end of the needle carrier and the second end of the needle extends beyond the second end of the needle carrier.

17. A needle protection device as claimed in claim 1, wherein said first end of the needle extends axially beyond the first end of the shuttle when the needle carrier is in the first deployed position and is contained within the shuttle when the needle carrier is in the second protected position.

18. A needle protection device as claimed in claim 1, wherein said second end of the needle extends into an inner void when the needle carrier is in the first deployed position and is contained within an aperture when the needle carrier is in the second protected position.

19. A needle protection device as claimed in claim 1, wherein in a first position of the needle carrier the second end of the needle extends into an inner void and in a second position does not extend into said inner void.

* * * * *